United States Patent
Hell (10) Patent No.: US 7,894,067 B2
(45) Date of Patent: Feb. 22, 2011

(54) METHOD AND APPARATUS FOR THE HIGH SPATIAL RESOLUTION IMAGING OF A STRUCTURE MARKED WITH A SUBSTANCE

(75) Inventor: Stefan Hell, Göttingen (DE)

(73) Assignee: Max-Planck-Gesellschaft zur Förderung der Wissenschaften e.V., München (DE)

( * ) Notice: Subject to any disclaimer, the term of this patent is extended or adjusted under 35 U.S.C. 154(b) by 76 days.

(21) Appl. No.: 12/486,224

(22) Filed: Jun. 17, 2009

(65) Prior Publication Data

US 2009/0279086 A1      Nov. 12, 2009

Related U.S. Application Data

(63) Continuation of application No. PCT/EP2007/010905, filed on Dec. 12, 2007.

(30) Foreign Application Priority Data

Dec. 18, 2006   (DE)   ................. 10 2006 060 180

(51) Int. Cl.
*G01N 21/25* (2006.01)
(52) U.S. Cl. .................................................. 356/417
(58) Field of Classification Search ......... 356/317–318, 356/417
See application file for complete search history.

(56) References Cited

U.S. PATENT DOCUMENTS 5,345,139 A    9/1994   Gururaja et al.

6,756,591 B1 *  6/2004   Lounis et al. .......... 250/339.14

(Continued)

FOREIGN PATENT DOCUMENTS

DE      94 08 282 U1    9/1994

(Continued)

OTHER PUBLICATIONS

Berciaud, S. et al: "Photothermal heterodyne imaging of individual metallic nanoparticles: Theory versus experiment" in: Pysical Review B 73, 045424-1-045424-8, (Jan. 20, 2006).

(Continued)

*Primary Examiner*—Kara E Geisel
(74) *Attorney, Agent, or Firm*—Thomas, Kayden, Horstemeyer & Risley, LLP (57) ABSTRACT

For the high spatial resolution imaging of a structure in a sample (2) the structure is marked with a substance which can be changed over by means of a first electromagnetic signal (5) from a first state having a larger absorption cross section for a second electromagnetic signal (3) into a second state having a smaller absorption cross section for the second signal (3) or which can be changed over by means of a first electromagnetic signal (5) into a first state having a larger absorption cross section for a second electromagnetic signal (3) from a second state having a smaller absorption cross section for the second signal (3). A spatially delimited distribution of a portion of the substance in the first state is then set by means of the first signal (5). Afterward, the second electromagnetic signal (3) is applied to the sample (2), and a local temperature increase in the sample (2) which results from the larger absorption cross section of the substance in the first state is detected.

34 Claims, 2 Drawing Sheets

U.S. PATENT DOCUMENTS

| | | | |
|---|---|---|---|
| 6,909,105 | B1 | 6/2005 | Heintzmann et al. |
| 2002/0126732 | A1* | 9/2002 | Shakouri et al. ............ 374/130 |
| 2004/0188602 | A1 | 9/2004 | Chinn et al. |
| 2004/0212799 | A1 | 10/2004 | Hell |

FOREIGN PATENT DOCUMENTS

| | | |
|---|---|---|
| DE | 103 25 460 A1 | 11/2004 |
| EP | 1 157 297 B1 | 11/2001 |

OTHER PUBLICATIONS

Boyer, D. et al: "Photothermal Imaging of Nanometer-Sized Metal Particles Among Scatters" in: Science vol. 297, 1160-1163 (Aug. 16, 2002).

Tamaki, E. et al: "Single-Cell Analysis by a Scanning Thermal Lens Microscope with a Microchip: Direct Monitoring of Cytochrome c Distribution during Apoptosis Process" in Analytical Chemistry, vol. 74, No. 7, 1560-1564 (Apr. 1, 2002).

Search Report and International Preliminary Report of Patentability from co-pending, co-related PCT Application No. PCT/EP2007/010905, dated Jul. 7, 2009.

Egner, A. et al: "4Pi-microscopy of the Golgi apparatus in live mammalian cells." in: Journal of Structural Biology, 2004, vol. 147, p. 70-76.

* cited by examiner

METHOD AND APPARATUS FOR THE HIGH SPATIAL RESOLUTION IMAGING OF A STRUCTURE MARKED WITH A SUBSTANCE

CROSS-REFERENCE TO RELATED APPLICATIONS

This application is a continuation of the international patent application PCT/EP2007/010905 entitled "Spatial high Resolution of a Structure", filed on Dec. 12, 2007 and claiming the priority of German patent application No. DE 10 2006 060180.7, which is entitled "Verfahren und Vorrichtung zum räumlich hochaufgelösten Abbilden einer mit einer Substanz markierten Struktur" ["Method and apparatus for the high spatial resolution imaging of a structure marked with a substance"], was filed on Dec. 18, 2006 and is pending in parallel.

FIELD OF THE INVENTION

The invention relates to a method and an apparatus for the high spatial resolution imaging of a structure in a sample. In particular, the invention relates to a method and an apparatus for the high spatial resolution imaging of a structure in a sample wherein the structure is marked with a substance selected from a group of substances which can be changed over by means of a first electromagnetic signal from a first state, in which they have a larger absorption cross section for a second electromagnetic signal, into a second state, in which they have a smaller absorption cross section for the second electromagnetic signal, or which can be changed over by means of a first electromagnetic signal into a first state, in which they have a larger absorption cross section for a second electromagnetic signal, from a second state, in which they have a smaller absorption cross section for the second electromagnetic signal.

The high spatial resolution imaging of a structure in a sample is taken to mean here, in particular, the imaging of the structure with a spatial resolution that is better than the diffraction limit such as is applicable to conventional methods appertaining to light microscopy.

BACKGROUND OF THE INVENTION

US 2004/0212799 A1 discloses a method for the high spatial resolution imaging of a structure in a sample wherein a substance for marking the structure in the sample is selected from a group of substances which can be changed over by means of a first electromagnetic signal from a first state, in which it has first spectral properties, apart from a region deliberately omitted by the first electromagnetic signal, into a second state, in which it has second spectral properties. Various possibilities are specified for the two spectral properties of the substance. The possibility of the different spectral properties, as also mentioned in the exemplary embodiments described in greater detail in US 2004/0212799 A1, is a first state, in which the substance is fluorescent, and a second state, in which it is non-fluorescent. In order to image the structure in the sample, the fluorescence of the substance is excited by means of a second electromagnetic signal, and the fluorescent light emitted by the substance is detected. In this case, the fluorescent light from the substance can only originate from that region of the sample which is deliberately omitted by the first electromagnetic signal and in which the substance is still in the first state. If said region is for example the zero of an interference pattern of the first electromagnetic signal, it can be made smaller than the diffraction limit that is applicable to the imaging of the sample with light having the wavelength of the first or of the second electromagnetic signal. Among the further possibilities for the two different spectral properties of the substance in the first state and the second state which are discussed in US 2004/0212799 A1, the indication about a different absorption for a second optical signal in the form of a test beam is claimed. However, no further details are found with regard to this variant—corresponding to the preamble of independent patent claim 1—of the known method and the apparatus implicitly disclosed thereby with the features of the preamble of independent patent claim 16.

In order to implement the basic concept known from US 2004/0212799A1 of using an electromagnetic signal to set a spatial distribution of a portion of the substance in a fluorescent state in the case of which the regions in which the substances is present in the fluorescent state are spatially delimited, it is also known for an electromagnetic signal which changes over the substance from a non-fluorescent state into a fluorescent state to be applied to the sample in an intensity such that afterward only individual molecules of the substance are in the fluorescent state, which are imaged separately from one another during a microscopic imaging of the fluorescent light emerging from them. It is thus established that the portions of the fluorescent light from the sample which are detected separately from one another in each case originate from individual molecules whose position can be determined from the centroid of the intensity distribution of the fluorescent light with a higher spatial resolution than the diffraction limit at the wavelength of the fluorescent light. This technique is known not only by the name SPARSE but also by the name STORM or PALM, while the name RESOLFT is used for the technique known from US 2004/0212799 A1.

Methods appertaining to fluorescence microscopy have the known fundamental disadvantage of the bleaching of the fluorescent dyes used. This means that a fluorescent dye can only undergo a finite number of excitation and fluorescence emission cycles, usually fewer than 100 000, before it incurs an undesirable chemical conversion into a state that is permanently no longer fluorescent. This problem also occurs in the case of the RESOLFT and SPARSE techniques described above. An additional factor is that the first electromagnetic signal used to set the spatial distribution of the portion of the substance in the fluorescent state can likewise lead to a burdening and thus possibly earlier bleaching of the substance. Some embodiments of the SPARSE technique therefore provide for bringing the individual molecules of the substance into the fluorescent state only once by means of the first signal and then in that state exciting them to fluorescence until the individual molecule is bleached.

In addition, besides the absolute yield of fluorescent light from a molecule of a fluorescent dye, the quantity of fluorescent light that is obtainable therefrom during a specific period of time is also limited. A molecule of a fluorescent dye can only ever be excited to fluorescence by excitation light when it is in its ground state. Until a next possible excitation it is therefore necessary to wait until the molecule has reverted to its ground state. The fact of whether it emits fluorescent light at all in the event of this reversion to its ground state depends on the ratio of its transition probabilities. Often the emission of fluorescent light occurs in less than 50% of the excitations. The probability with which a fluorescent photon is detected is determined by the respective measurement setup; this value is usually even less than 10%. In order to detect evaluable quantities of fluorescent light, therefore, in many cases long measurement times have to be accepted, in general they are more than 10 μs per pixel or fluorescent molecule. These measurement times accumulate particularly in the case of highly localized portions of the fluorescent dye in the fluorescent state or even individual fluorescent molecules until a complete image of the structure of interest in the sample is created. Long measurement times are not just uneconomic in principle, but regularly pose problems with drifting of various components of the measurement setup used.

As an alternative to marking a structure in a sample with a fluorescent substance, it is known from S. Berciaud et al.: "Photothermal heterodyne imaging of individual metallic nanoparticles: Theory versus experiment" in PHYSICAL REVIEW B 73, 045424 (2006) to mark the structure with gold nanoparticles. In order to visualize the marked structure, a method referred to as photothermal heterodyne imaging (PHI) is described, which is based on an increase in the temperature of the sample by an individual nanoparticle on account of the absorption of an electromagnetic signal by a gold nanoparticle situated in the respective measurement region. The electromagnetic signal absorbed by the gold nanoparticle is converted into heat. This brings about a local temperature increase in the sample at the location of the nanoparticle. In specific terms, a temperature gradient pointing away from the nanoparticle is formed. This temperature gradient affects the phase of a test beam which passes through the sample and which is used in addition to the electromagnetic signal which is absorbed by the gold nanoparticles and thus increases the temperature thereof. For detecting the phase shift on account of a local temperature increase, in order to determine the size and possibly also the position of the temperature increase, the PHI technique involves using a frequency-modulated laser beam for heating the gold particles, which leads to a frequency-modulated phase shift of the test beam, which can easily be detected upon comparison with the non-phase-shifted test beam. It is thereby intended to be possible to detect gold nanoparticles down to a size of 1.4 nm (67 atoms).

Other methods for detecting local temperature increases on account of absorbent gold nanoparticles encompass other forms of far field interference microscopy wherein different portions of a test beam, only one of which portions has passed through the region of the temperature increase, are brought to interference with one another (see D. Boyer et al.: "Photothermal Imaging of Nanometer-Sized Metal Particles Among Scatterers" in Science Vol. 297, pp. 1160-1163 (Aug. 16, 2002).

The effect known as thermal lens can also be used for the microscopic detection of a local temperature increase caused by absorption, wherein here the electromagnetic signal that causes the temperature increase on account of its absorption and the test beam that is phase-shifted owing to the resulting temperature gradient are identical (see E. Tamaki et al.: "Single-Cell Analysis by a Scanning Thermal Lens Microscope with a Microchip: Direct Monitoring of Cytochrome c Distribution during Apoptosis Process" in Analytical Chemistry, Vol. 74, No. 7, pp. 1560-1564 (Apr. 1, 2002)).

There is still a need for a method and an apparatus for the high spatial resolution imaging of a structure in a sample which enable a better spatial resolution of the structure in the sample than the diffraction limit, without accepting the known disadvantages of the use of fluorescent dyes.

SUMMARY OF THE INVENTION

In one aspect, the invention provides a method for the high spatial resolution imaging of a structure in a sample comprising the following steps: selecting a substance from a group of substances, wherein the group of substances comprises substances which can be changed over by means of a first electromagnetic signal from a first state, in which they have a larger absorption cross section for a second electromagnetic signal, into a second state, in which they have a smaller absorption cross section for the second electromagnetic signal, and substances which can be changed over by means of a first electromagnetic signal into a first state, in which they have a larger absorption cross section for a second electromagnetic signal, from a second state, in which they have a smaller absorption cross section for the second electromagnetic signal; marking the structure with the selected substance; setting a spatial distribution of a portion of the substance in the first state by means of the first electromagnetic signal, wherein at least one region in which the substance is present in the first state is spatially delimited in the distribution; applying the second electromagnetic signal to the sample having the set spatial distribution of the portion of the substance in the first state; and detecting at least one local temperature increase in the sample which results from the larger absorption cross section of the substance in the first state upon application of the second electromagnetic signal.

In another aspect, the invention provides an apparatus for the high spatial resolution imaging of a structure in a sample marked with a substance selected from a group of substances, wherein the group of substances comprises substances which can be changed over by means of a first electromagnetic signal from a first state, in which they have a larger absorption cross section for a second electromagnetic signal, into a second state, in which they have a smaller absorption cross section for the second electromagnetic signal, and substances which can be changed over by means of a first electromagnetic signal into a first state, in which they have a larger absorption cross section for a second electromagnetic signal, from a second state, in which they have a smaller absorption cross section for the second electromagnetic signal, wherein the apparatus has: a first signal source for the first electromagnetic signal, said first signal source being embodied and arranged in such a way that it sets a spatial distribution of a portion of a substance in the first state in the case of which at least one region in which the substance is present in the first state is spatially delimited; a second signal source for the second electromagnetic signal, said second signal source being embodied and arranged in such a way that it applies the second electromagnetic signal to the sample after the setting of the spatial distribution of the portion of the substance in the first state; and a detector, which is embodied and arranged in such a way that it detects at least one local temperature increase in the sample which results from the larger absorption cross section of the substance in the first state.

In the novel method, the structure in the sample is marked with a substance which can be changed over by means of a first electromagnetic signal from a first state into a second state, or vice-versa, wherein the substance has a higher absorption cross section for a second electromagnetic signal in the first state than in the second state. Said second electromagnetic signal is applied to the sample after a spatial distribution of a portion of the substance in the first state in the case of which at least one region in which the substance is present essentially in the first state is spatially delimited has been set by means of the first electromagnetic signal. In this case, it is not necessary for the second electromagnetic signal to be localized to specific regions of the sample. The spatial delimitation is already effected beforehand by means of the first electromagnetic signal. The absorption of the second electromagnetic signal by those portions of the substance which are in the first state leads, in the region thereof, to a local temperature increase in the sample. This is detected in the novel method, instead of attempting to directly detect the different absorption of the substance by means of a test beam.

The local temperature increase in the sample when the second electromagnetic signal is applied to the sample on account of the larger absorption cross section of the substance in the first state can be detected by all techniques known as such for detecting local temperature increases. These include all methods for photothermal imaging as described under the heading prior art. In other words, the at least one local temperature increase in the sample can be in particular detected on the basis of a phase shift—associated therewith—of an electromagnetic signal passing through the sample. Said phase shift is based on the refractive index change in the sample that is associated with the temperature increase. In principle, however, it is also possible to detect scattered light that arises as a result of said refractive index change in the sample.

Said electromagnetic signal whose phase shift is observed can be an additional third electromagnetic signal, which differs in its wavelength from the first and the second electromagnetic signal. However, it is also possible to observe the first or the second electromagnetic signal with regard to phase shifts that occur. In the case of the second electromagnetic signal, a similar configuration as in the technique known as thermal lens is then present.

Typically, at least one of the electromagnetic signals mentioned here is a monochromatic optical signal. Often, all the electromagnetic signals used will be monochromatic optical signals.

A particularly high sensitivity with regard to local temperature increases in the sample is afforded by the techniques of optical field interference microscopy as described under the heading prior art, which also include the PHI technique.

Preferably, what is involved is not just binary registration of whether or not a local temperature increase is present in a region of the sample, rather the magnitude of said temperature increase is also determined in order thus to obtain an indication about the quantity of the substance in the first state in the respective region.

As an alternative or in addition, a position of the local temperature increases in the sample can be registered. If it is established or assumed that the distribution of the substance that causes the temperature increase within the respective region is constant and the region itself is sufficiently small, it is possible to determine therefrom the position of the substance in the sample and hence a part of the structure of interest with a spatial resolution better than the diffraction limit at the wavelength of the electromagnetic signal with which the temperature increase is detected. In this case, the centroid of the position of the temperature increase in the sample is equated to the position of the substance in the first state.

However, if the substance is left in the first state or changed over thereto by means of the first electromagnetic signal in regions of the sample that are known as such, it is more favorable to use the position of these regions as the position of the substance that causes the temperature increase, and to additionally register only the size of the temperature increase in order to obtain a measure of the amount of substance in the respective region.

In the case of the present invention, although it would be desirable for the substance to have a very large absorption cross section for the second electromagnetic signal in the first state and an absorption cross section for said signal of zero in the second state, this is not mandatory. Moreover, it suffices for the substance to be selected from a group of substances which have an absorption cross section for the second electromagnetic signal which is at least ten times, preferably at least one hundred times, larger in the first state than in the second state. The temperature gradient formed on account of the second electromagnetic signal of the sample rises with the absorption cross section of the substance for the second electromagnetic signal.

The refractive index change in the sample which is associated with the temperature increase and which can be detected by the phase shift of a signal passing through the sample, or alternatively by scattered light, all the better, the greater it is, depends not only on the absorption cross section for the second electromagnetic signal and hence the absolute temperature change but also on the specific refractive index change in the sample with temperature. Therefore, it is advantageous to embed the sample to be examined into a medium in which the temperature increase is associated with a particularly high refractive index change. Thus, many organic liquid media have a refractive index reduction of 0.0005 per 1 K temperature increase, whereas water has only a refractive index reduction of 0.0001 per 1° C. As an alternative or in addition, the sample can be set to such a temperature at which the temperature increase brought about by the second electromagnetic signal, in the medium present, brings about a refractive index jump that is as large as possible. Thus, in the case of aqueous samples it is advantageous to cool the sample, wherein a sample temperature of −10 to 5° C. is particularly favorable with regard to a large refractive index change in the event of a temperature change.

For the present invention in practise, in particular those substances which can be changed over from the first state into the second state repeatedly by means of the first electromagnetic signal are preferred. This makes it possible to set, by means of the first optical signal, a spatial distribution of a portion of the substance in the first state in the case of which only those portions of the substance which are situated at the location of a zero of the first electromagnetic signal that is formed by destructive superposition are in the first state, in order to scan the entire sample using one or more of the zeros of the first signal that are formed in this way. The zero formed by destructive superposition of the first signal with itself can be a zero of an interference pattern. A particularly preferred zero of this type is the center of a donut-shaped intensity distribution of the first optical signal.

If in each case only individual mutually spatially separate molecules or clusters of molecules of the substance used to mark the structure in the sample are changed over into the first state, it may be sufficient for the substance to be selected from a group of substances which can be changed over from the second state into the first state just once by means of the first electromagnetic signal. If it no longer reverts to the second state, it then has to be able, however, to be changed over from the first state into a third state, in which its absorption cross section is again smaller than in the first state. When such a substance is used, by means of the first optical signal, a spatial distribution of a portion of the substance in the first state is set in the case of which only individual molecules or clusters of molecules of the substance are in the first state which are spaced apart from one another to such an extent that the local temperature increase in the sample which proceed from them when the second signal is applied to the substance can be detected separately from one another in an imaging onto a two-dimensional photosensor, such as e.g. a camera. Each temperature increase can then be assigned to an individual molecule or cluster of molecules and the position of this individual molecule or cluster of molecules can be registered from the position of the temperature increase in the sample with a better spatial resolution than the diffraction limit.

In one specific embodiment of the present invention that is oriented to the concept of the SPARSE technique, only a single electromagnetic signal is directed onto the respective sample. This signal is absorbed by individual molecules or clusters of molecules of the substance used to mark the structure of interest in the sample which have entered into the absorbent first state spontaneously, that is to say on account of thermal excitation already at the initial temperature of the sample, and/or owing to the global heating of the sample by the one electromagnetic signal. The one electromagnetic signal also serves for detecting the resultant local temperature increases in the sample and ultimately changes over the molecules or clusters of molecules of the substance measured in this way into a third state in the sense of bleaching, in which third state the substance no longer absorbs the electromagnetic signal and from which third state the substance also no longer returns to the absorbent second state. Although an additional first electromagnetic signal that is directed onto the sample in order to be used to set the portion of the substance in the sample in the first absorbent state is then omitted, it can be seen in the thermal excitation of the sample. If said thermal excitation is based on the one electromagnetic signal, which is then also absorbed by the substance in the first state, this one electromagnetic signal represents both the first and the second electromagnetic signal within the meaning of the patent claims.

In particular, photochromic dyes are appropriate as a substance for marking the structure of the sample, said photochromic dyes having a greatly altered absorption cross section for the second signal where their state is altered by means of the first signal.

The substance can also be selected from a group of substances which additionally have different fluorescence properties in the first state than in the second state. Preferably, the substances involved here are those which are weakly fluorescent in the first state and are non-fluorescent in the second state. In this case, the second electromagnetic signal or alternatively a different electromagnetic signal can excite the substance to emit fluorescent light, with which the distribution of the substance or the structure marked thereby in the sample can be imaged via a second channel.

Particularly preferably, the second electromagnetic signal is applied to the sample in pulses having a high intensity density, wherein the temporary local temperature increase in the sample is detected directly after each pulse of the second electromagnetic signal. In this way it is possible to temporarily form in the sample a very high temperature gradient on account of the local temperature increase in the sample. Correspondingly, the effect is particularly large with regard to the phase shift of the electromagnetic signal used for detecting the local temperature increase. At the same time, however, on average only little thermal energy is input into the sample by the pulsed second electromagnetic signal, with the result that it is also possible to observe living biological samples without thermally destroying the latter.

In principle, the second electromagnetic signal can also be modulated if it is applied to the sample, in order thereby to provide the preconditions for application of the PHI technique.

The novel apparatus has a detector, which can detect at least one local temperature increase in the sample that results from the larger absorption cross section of the substance in the first state when the second electromagnetic signal is applied. The novel apparatus has corresponding signal sources for the first and second electromagnetic signals. In addition, it is possible to provide a third signal source for a third electromagnetic signal, on the basis of the phase shift of which the detector detects the local temperature increases in the sample. However, the detector can also be provided for using the first or the second electromagnetic signal from the first or second signal source, respectively, for this purpose.

The signal sources are preferably those which supply monochromatic optical signals, for example in the form of laser beams. In this case, in most of the embodiments of the present invention the first and the second signal, in the same way as a possible third signal, differ in terms of different wavelengths.

Further aspects of the novel apparatus have already been explained on the basis of the novel method.

If the sample is intended to be temperature-regulated to a specific temperature at which it has a particularly high specific refractive index change with temperature, it is necessary to provide a temperature-regulating device for the sample for this purpose. If the structure in the sample is additionally intended to be imaged with fluorescent light from the substance in the first state, then it is necessary to provide a fluorescent light detector for the spatially resolved detection of fluorescent light from the sample. Said fluorescent light detector can be combined with the detector for detecting local temperature increases in the sample.

Advantageous developments of the invention emerge from the dependent patent claims and the entire description. Further features can be gathered from the drawings—in particular the illustrated geometries and the relative dimensions of a plurality of component parts with respect to one another and also their relative arrangement and operative connection. The combination of features from different embodiments of the invention or of features from different patent claims in a departure from the references back chosen is likewise possible and is hereby suggested. This also concerns those features which are illustrated in separate figures in the drawings or are mentioned in the description thereof. These features can also be combined with features from different patent claims.

BRIEF DESCRIPTION OF THE FIGURES

The invention will be understood better with the following drawings being taken into account. The parts in the drawings are not necessarily reproduced true to scale; rather, importance is attached to clearly illustrating the principles of the present invention. In the drawings, identical reference symbols designate identical parts in the various views.

DETAILED DESCRIPTION

S. Berciaud et al.: "Photothermal heterodyne imaging of individual metallic nanoparticles: Theory versus experiment" in PHYSICAL REVIEW B 73, 045424 (2006) have reported that gold nanoparticles having a size of 1.4 nm (67 atoms) can be detected by the PHI technique. The absorption cross section of photochromic dyes at the wavelength maximally absorbed by them is of the same order of magnitude as that of gold atoms in a cluster. Accordingly, at least those regions of a structure marked with a photochromic dye which have a few 10 molecules of the photochromic dye in the first state can be photothermally imaged in accordance with the novel method. At a sufficiently high concentration of the photochromic dye, this condition is noncritical even when the photochromic dye in the sample is changed over by means of the first electromagnetic signal from the first state into the second state with the smaller absorption cross section apart from a region, in each case, which has smaller dimensions than the diffraction limit. All that is important in that case is that in the respective region, the structure in the sample is marked if appropriate with more than approximately a few 10 dye molecules.

Although individual conventional dye molecules in the more highly absorbent first state had not as yet been detected by known photothermal imaging techniques, it nevertheless appears to be possible to select photochromic dyes having a particularly large absorption cross section of an individual molecule and also to form clusters of photochromic dye molecules which are changed over by means of the first signal from the second state into the more highly absorbent first state either as a whole or not at all. Furthermore, it appears to be possible to maximize the refractive index change associated with a temperature increase by optimized selection of the medium and the temperature thereof. Furthermore, it can be assumed that the sensitivity of photothermal imaging techniques will increase further, to be precise by the use of even more sensitive detectors and of electromagnetic signals which are better adapted to the requirements of the temperature measurement. It is thus possible, in practise, for the novel method also to be carried out in the form of a variant of the SPARSE technique in which the individual molecules or clusters of molecules are changed over to the more highly absorbent state by means of the first signal which are so far away from one another that they are imaged separately from one another during photothermal imaging onto a two-dimensional photosensor.

Figure 1:
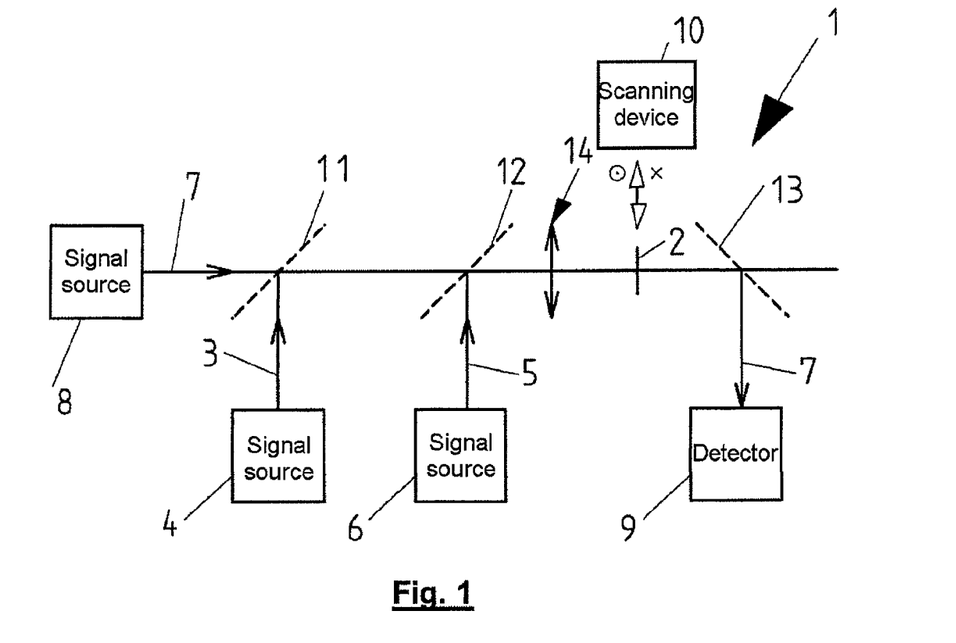
FIG. 1 shows the basic construction of a first embodiment of the novel apparatus for carrying out the novel method with three signal sources.

Referring now in greater detail to the drawings, FIG. 1 shows the basic construction of an apparatus 1 for carrying out the novel method. In other words, the apparatus 1 serves for imaging a structure in a sample 2. The structure (not represented separately here) in the sample 2 is in this case marked with a substance, here a photochromic dye, which has two states. An absorption cross section of each molecule is much larger, that is to say at least ten times, preferably at least one hundred times, larger, in the first state than in its second state. These different absorption cross sections relate to an electromagnetic signal 3, which is a monochromatic optical signal in the form of a laser beam, from a signal source 4, that is to say a laser. The photochromic dye can be changed over from its first state having the large absorption cross section by means of an electromagnetic signal 5, which is likewise a monochromatic optical signal in the form of a laser beam from a signal source 6, that is to say a laser. In this case, the changeover is effected in a respective measurement region of the sample 2 apart from a region currently of interest, with the result that the photochromic dye is in its state having the large absorption cross section only in said region of interest. For this purpose, the electromagnetic signal 5 is superposed with itself in the region of the sample 2 in such a way that it forms a zero of its intensity distribution at the location of the region of interest, while it covers the further measurement region with such a high intensity that the dye is changed over into its second state with high probability. In specific terms, the intensity distribution of the electromagnetic signal 5 in the region of the sample 2 can be donut-shaped, the center of the donut containing the zero of the intensity distribution of the electromagnetic signal 5. If the electromagnetic signal 3 from the signal source 4 is now applied to the measurement region, the signal 3 can be absorbed only by those molecules of the photochromic dye which are situated in the region of the zero of the intensity distribution of the electromagnetic signal 5, since all the other molecules of the photochromic dye in the measurement region have been changed over into the non-absorbent state by means of the electromagnetic signal 5. This results in a local temperature increase in the sample 2, which is dependent on the concentration of the photochromic dye in the region of the zero of the intensity distribution of the electromagnetic signal 5. Said local temperature increase is photothermally imaged in the apparatus 1 by means of a further electromagnetic signal 7 again in the form of a monochromatic optical signal, in specific terms a laser beam from a signal source 8, that is to say a laser, being directed onto the sample 2. The electromagnetic signal 7 passes through the measurement region in the sample 2 and impinges on a detector 9 downstream of the sample 2. The detector 9 registers whether a phase shift of the electromagnetic signal 7 arises on account of a temperature gradient in the sample 2 that is attributable to a local temperature increase in the sample 2 on account of the absorption of the electromagnetic signal 3 at the location of the zero of the intensity distribution of the electromagnetic signal 5. The detector 9 can also register the magnitude of the gradient and thus the magnitude of the temperature increase and thus ultimately the concentration of the photochromic dye at the location of the zero of the electromagnetic signal 5. If the sample 2 is displaced two-dimensionally by means of a scanning device 10 in such a way that the entire sample 2 has been scanned with the zero of the intensity distribution of the electromagnetic signal 5, where it is also possible to provide a multiplicity of such zeros, an image of the intensity distribution of the photochromic dye in the sample 2 arises. The structure marked with the photochromic dye in the sample is imaged in this way.

Compared with the use of a fluorescent dye, in this case considerable advantages are afforded with regard to the magnitude and thus the signal-to-noise ratio of the measurement signal. A molecule of a fluorescent dye can only ever be excited to fluorescence by means of excitation light when it is in its ground state. Until a next possible excitation, which can take place at the earliest after 1 to 5 ns, it is necessary to wait until the molecule has reverted to its ground state. The fact of whether it emits fluorescent light upon this reversion to its ground state depends on the ratio of its transition probabilities; the fluorescence quantum efficiency of the excitation is usually less than 50%. An additional factor is that the fluorescent molecule regularly becomes trapped in a long-lived dark state, such as the triplet state, for example, in which it is stays for 1 μs to a few seconds without being able to contribute to the fluorescence signal. The probability with which the fluorescent light is actually detected in the apparatus depends on the respective measurement setup; it usually amounts to less than 10%. In any event the yield of photons per molecule of the fluorescent dye per unit time is narrowly limited. Added to this is the risk of the fluorescent dye being bleached on account of the multiple excitation by the excitation light. By contrast, in the case of the novel method outlined here, although the photochromic dye is also excited by means of the electromagnetic signal 3, this excitation is converted into heat very quickly (within less than 2 ps) and each dye molecule is thus immediately available again for a renewed excitation with the electromagnetic signal 3. The ultrafast relaxation of the molecule counteracts a chemical alteration since the latter can take place only from an excited state, but said excited state already decays within less than 2 ps. Thus, in an extremely short time, a large number of photons from the second electromagnetic signal can be absorbed and a local temperature increase can be brought about in the sample 2. By way of example, the electromagnetic signal 3 can be pulsed, and during each pulse a multiplicity of excitations of each dye molecule in the absorbent state are already effected, resulting in a temperature increase in the sample, which can be detected after each individual pulse. In order to detect this temperature increase, a much stronger signal than is provided by fluorescent light is likewise used with the electromagnetic signal 7.

All the essential advantages which are associated with the marking of a structure in a sample using a fluorescent dye are maintained in this case. The selective marking of a specific cell constituent, such as a protein, is furthermore provided by the specificity of the substance. Moreover, multiple markings can be carried out since markers having different absorption spectra can be chosen. It is likewise possible to use cell-endogenous markings, such as proteins or protein sections, for example, which have a particularly high absorption at specific wavelengths. One of the most important markers in fluorescence microscopy, in particular for living cells, is the green fluorescent protein (GFP) and the derivatives derived therefrom, since they can be biochemically fused virtually to any protein. In the case of fluorescent proteins it is important that these are optimized for high fluorescence quantum efficiency, that is to say that the excitation energy is converted as far as possible into fluorescent light and not into heat—which is rather difficult to accomplish. On the contrary, collisions with the surroundings of the molecule (e.g. water molecules) lead to a conversion of the excitation energy into heat that is undesirably efficient in fluorescence microscopy. It is therefore much more difficult to produce or find a protein exhibiting good fluorescence than a non-fluorescent protein, that is to say one which converts the excitation energy into heat well. This also applies to photochromic (switchable) proteins. One advantage of the invention described here is that this disadvantage is converted into an advantage, since the conversion into heat is even desired here. It not only leads to the rapid heating of the microenvironment of the substance in the sample, but rapidly returns the molecule to the absorbent ground state, in which it can once again take up energy from the electromagnetic signal 3. It is likewise rather more difficult to find organic fluorescent markers which are both switchable and fluorescent, since most optically switchable (photochromic) organic compounds are not fluorescent, but rather only change their absorption spectrum. By contrast, they can efficiently convert their energy into heat.

Nevertheless, upon application of the present invention it can be advantageous to select a substance for the marking of the structure in the sample which still has a measurable quantum efficiency of fluorescence alongside a high conversion rate of the absorbed photon energy into heat in its first state. A further measurement channel in which the substance can be detected by fluorescence imaging is thus available.

With proper tuning of the wavelengths of the electromagnetic signals 3 and 7 and also 5, there is no appreciable risk of bleaching of the photochromic dye despite the multiple excitation upon absorption of the electromagnetic signal 3, owing to the only very short lifetime of the excited state.

The reversion of the photochromic dye from its second state back into its first state, which has to take place rapidly enough that the sample 2 can be scanned by means of the scanning device 10, takes place spontaneously here. However, it can be excited by a further electromagnetic signal (not shown here). It is likewise conceivable for one of the electromagnetic signals 3 and 7 to excite this reversion.

For combining or separating the different electromagnetic signals 3, 5 and 7, the apparatus 1 has dichroic mirrors 11, 12 and 13 coordinated with the respective wavelengths. An objective 14 focuses the electromagnetic signals 3, 5 and 7 onto the sample 2. A further objective (not illustrated here) is regularly also provided between the sample 2 and the detector 6.

Figure 2:
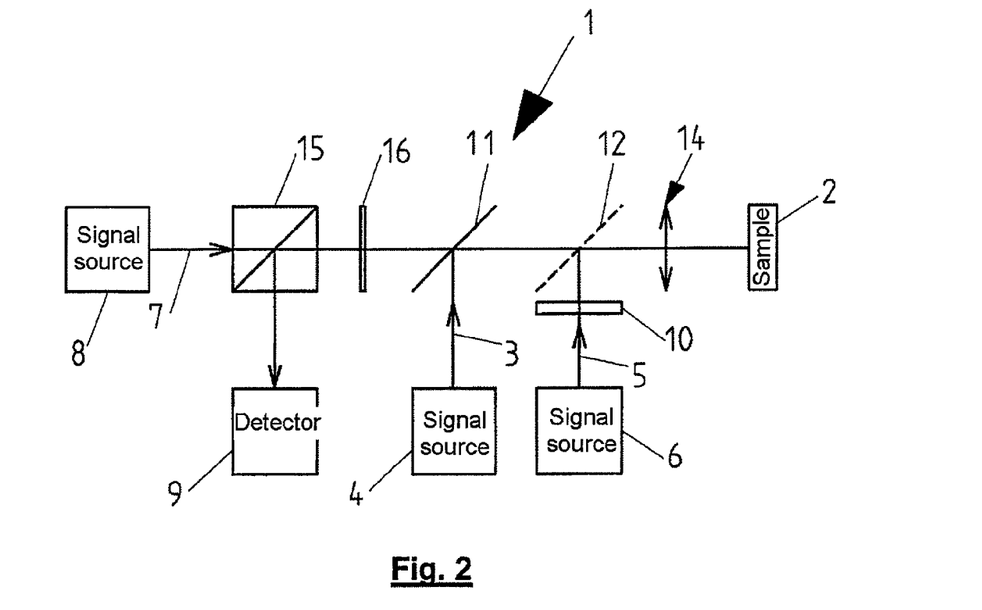
FIG. 2 shows a second embodiment of the novel apparatus for carrying out the novel method, likewise with three signal sources.

While FIG. 1 has the detector 9 downstream of the sample 2 with respect to the signal sources 4, 6 and 8, in the embodiment of the apparatus 1 in accordance with FIG. 2 said detector is not provided in a transmission arrangement but rather in a reflection arrangement. In this case, a polarizing beam splitter 15 in conjunction with a lambda/4 plate 16 is provided for deflecting the reflected electromagnetic signal 7 to the detector 9. In this case, by means of a modulator (not illustrated here), the electromagnetic signal 3 can be modulated with regard to its intensity over time in order to provide the preconditions for a PHI technique during thermal imaging of the local temperature increases in the sample 2. Furthermore, the scanning device 10 is embodied here in such a way that it does not move the sample 2 with respect to the electromagnetic signals 3, 5 and 7, but rather moves the electromagnetic signal 5, which defines the region of the dye in the absorbent state, with respect to the sample 2. For this purpose, the scanning device 10 can have for example an optical element moved by a galvanometer scanner or alternatively a so-called spatial light modulator and the respectively associated further components of such a scanning device that are known to the person skilled in the art, in particular lenses for adapting the imaging. Otherwise, however, the functioning of the apparatus 1 in accordance with FIG. 2 is in principle the same as that in accordance with FIG. 1.

Figure 3:
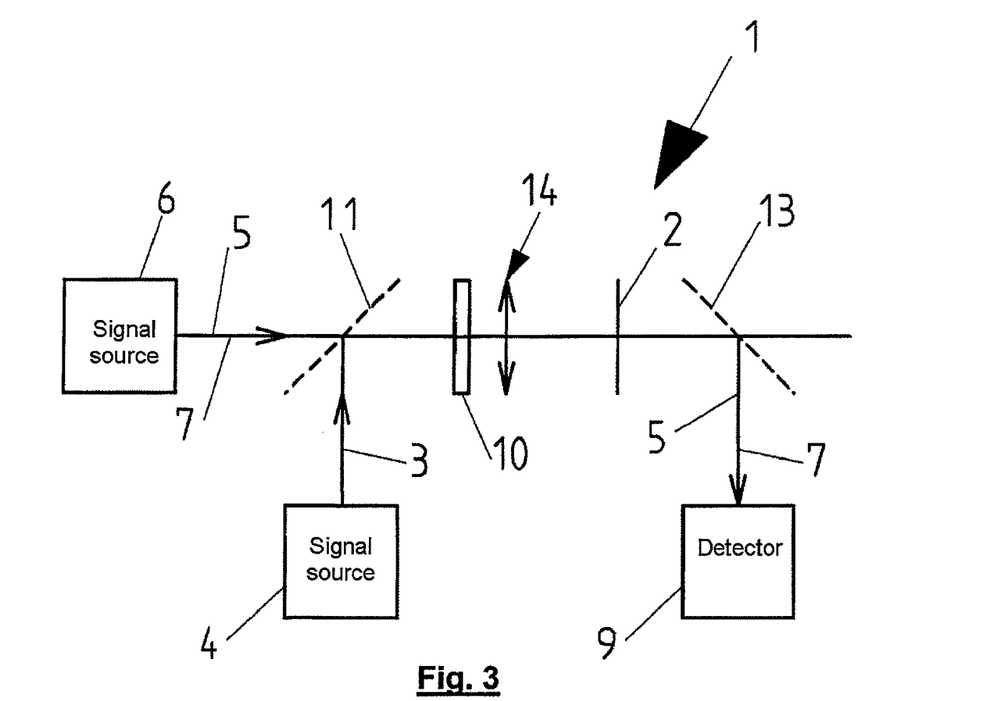
FIG. 3 shows a third embodiment of the novel apparatus for carrying out the novel method with two signal sources.

The apparatus 1 in accordance with FIG. 3 has the detector 9 in a transmission arrangement again. Moreover, a separate signal source 8 for the electromagnetic signal 7 is dispensed with here. Instead, here the local temperature increase in the sample 2 is detected by the electromagnetic signal 5 being observed with regard to phase shifts by means of the detector 9. In specific terms, the detector 9 can detect whether a donut-shaped intensity distribution of the electromagnetic signal 5 in the region of the sample 2 deforms on account of the electromagnetic signal 3, that is to say on account of a local temperature increase resulting therefrom. In this case, the electromagnetic signal 3 can again be modulated in order to ascertain whether there is a corresponding modulation of the electromagnetic signal 5 downstream of the sample 2, which modulation indicates a modulated local temperature increase in the sample 2 or a modulated temperature gradient in the sample 2. In this case, the magnitude of the modulation of the electromagnetic signal 5 downstream of the sample 2 gives an indication of the magnitude of the temperature increase and thus of the concentration of the photochromic dye in the region of the zero of the intensity distribution of the electromagnetic signal 5. Here the scanning device 10 is arranged directly behind the objective 14 as seen from the sample 2 and synchronously moves all of the electromagnetic signals 3, 5 and 7, which are directed onto the sample 2, with respect to the sample 2. Thus, all of the electromagnetic signals 3, 5 and 7, which are directed onto the sample 2, can be concentrated on the respective measurement region of the sample 2.

Figure 4:
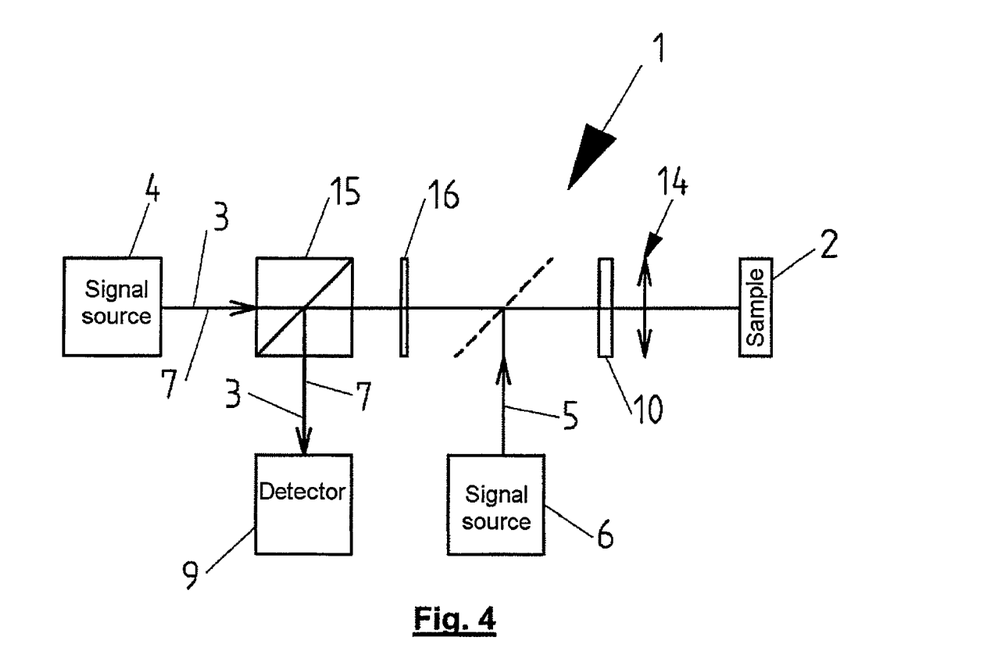
FIG. 4 shows a fourth embodiment of the novel apparatus for carrying out the novel method, likewise with two signal sources.

In the embodiment of the apparatus 1 in accordance with FIG. 4, the detector 9 is provided in a reflection arrangement as in FIG. 2. The polarization beam splitter 15 and the lambda/4 plate 16 are correspondingly provided here again. Here, however, the additional signal source 8 for the electromagnetic signal 7 is dispensed with by virtue of the fact that the electromagnetic signal 3, by means of which the sample 2 is initially heated locally where the photochromic dye is in its first, highly absorbent state, is also used for detecting this heating. An effect known as thermal lens is utilized in this case. The temperature gradient brought about by the electromagnetic signal 3 itself in the sample 2 effects a phase shift of the electromagnetic signal 3, which can be detected by the detector 9. The scanning device 10 is embodied in principle as in FIG. 3. In this case, here it also shifts the light coming back from the sample, with the result that said light always falls onto the same region of the detector 9 independently of the respective measurement region of the sample 2.

I claim:

1. A method for the high spatial resolution imaging of a structure in a sample comprising the following steps:
    selecting a substance from a group of substances, wherein the group of substances comprises
        substances which can be changed over by means of a first electromagnetic signal from a first state, in which they have a larger absorption cross section for a second electromagnetic signal, into a second state, in which they have a smaller absorption cross section for the second electromagnetic signal, and
        substances which can be changed over by means of a first electromagnetic signal into a first state, in which they have a larger absorption cross section for a second electromagnetic signal, from a second state, in which they have a smaller absorption cross section for the second electromagnetic signal;
    marking the structure with the selected substance;
    setting a spatial distribution of a portion of the substance in the first state by means of the first electromagnetic signal, wherein at least one region in which the substance is present in the first state is spatially delimited in the distribution;
    applying the second electromagnetic signal to the sample having the set spatial distribution of the portion of the substance in the first state; and
    detecting at least one local temperature increase in the sample which results from the larger absorption cross section of the substance in the first state upon application of the second electromagnetic signal.

2. The method as claimed in claim 1, wherein the at least one local temperature increase in the sample is detected on the basis of a phase shift—associated therewith—of an electromagnetic signal passing through the sample.

3. The method as claimed in claim 1, wherein the at least one local temperature increase in the sample is detected on the basis of a phase shift—associated therewith—of an electromagnetic signal passing through the sample, said electromagnetic signal being selected from the first electromagnetic signal, the second electromagnetic signal and an additional third electromagnetic signal.

4. The method as claimed in claim 1, wherein at least one of the electromagnetic signals is a monochromatic optical signal.

5. The method as claimed in claim 4, wherein the at least one local temperature increase in the sample is detected by optical far field interference microscopy.

6. The method as claimed in claim 1, wherein an extent of the at least one local temperature increase in the sample is registered.

7. The method as claimed in claim 1, wherein a spatial position of the at least one local temperature increase in the sample is registered.

8. The method as claimed in claim 7, wherein the centroid of the spatial position of the at least one local temperature increases in the sample is registered with a spatial resolution that is better than the diffraction limit.

9. The method as claimed in claim 1, wherein the substance is selected from a group of substances which have an absorption cross section for the second electromagnetic signal which is at least ten times larger in the first state than in the second state.

10. The method as claimed in claim 9, wherein the substance is selected from a group of substances which have an absorption cross section for the second electromagnetic signal which is at least one hundred times larger in the first state than in the second state.

11. The method as claimed in claim 1, wherein the substance is embedded into a medium that has a greater specific refractive index change with temperature than water.

12. The method as claimed in claim 11, wherein the substance is embedded into a liquid organic medium.

13. The method as claimed in claim 1, wherein the sample is temperature-regulated to a temperature at which it has a maximum refractive index change with temperature.

14. The method as claimed in claim 1, wherein the substance is selected from a group of substances which can be changed over from the first state into the second state repeatedly by means of the first electromagnetic signal.

15. The method as claimed in claim 14, wherein, by means of the first optical signal, a spatial distribution of a portion of the substance in the first state is set in the case of which only those portions of the substance which lie at a zero of the first signal that is formed by destructive superposition are in the first state.

16. The method as claimed in claim 1, wherein the substance is selected from a group of substances which can be changed over from the second state into the first state at least once by means of the first electromagnetic signal.

17. The method as claimed in claim 16, wherein, by means of the first optical signal, a spatial distribution of a portion of the substance in the first state is set in the case of which only individual molecules or clusters of molecules of the substance are in the first state which are spaced apart from one another to such an extent that the local temperature increases in the sample which proceed from them when the second signal is applied to the substance can be detected separately from one another in an imaging onto a two-dimensional photosensor.

18. The method as claimed in claim 1, wherein the substance is selected from the group of photochromic dyes.

19. The method as claimed in claim 1, wherein the substance is selected from a group of substances which additionally have different fluorescence properties in the first state than in the second state.

20. The method as claimed in claim 19, wherein the substance is selected from a group of substances which are fluorescent in the first state and are non-fluorescent in the second state.

21. The method as claimed in claim 1, wherein the second electromagnetic signal is applied to the sample in pulses of high intensity density, and the temporary local temperature increase in the sample is detected directly after each pulse of the second electromagnetic signal.

22. An apparatus for the high spatial resolution imaging of a structure in a sample marked with a substance selected from a group of substances, wherein the group of substances comprises
    substances which can be changed over by means of a first electromagnetic signal from a first state, in which they have a larger absorption cross section for a second electromagnetic signal, into a second state, in which they have a smaller absorption cross section for the second electromagnetic signal, and substances which can be changed over by means of a first electromagnetic signal into a first state, in which they have a larger absorption cross section for a second electromagnetic signal, from a second state, in which they have a smaller absorption cross section for the second electromagnetic signal, wherein the apparatus has:

a first signal source for the first electromagnetic signal, said first signal source being embodied and arranged in such a way that it sets a spatial distribution of a portion of a substance in the first state in the case of which at least one region in which the substance is present in the first state is spatially delimited;

a second signal source for the second electromagnetic signal, said second signal source being embodied and arranged in such a way that it applies the second electromagnetic signal to the sample after the setting of the spatial distribution of the portion of the substance in the first state; and a detector, which is embodied and arranged in such a way that it detects at least one local temperature increase in the sample which results from the larger absorption cross section of the substance in the first state.

23. The apparatus as claimed in claim 22, wherein the detector is embodied and arranged in such a way that it detects a phase shift of an electromagnetic signal passing through the sample, said phase shift being associated with the at least one local temperature increase in the sample.

24. The apparatus as claimed in claim 23, wherein the detector detects a phase shift of an electromagnetic signal passing through the sample, said electromagnetic signal being selected from the first electromagnetic signal, the second electromagnetic signal and an additional third electromagnetic signal.

25. The apparatus as claimed in claim 22, wherein at least one of the electromagnetic signals from one of the signal sources is a monochromatic optical signal.

26. The apparatus as claimed in claim 25, wherein the detector has the construction of a far field interference microscope.

27. The apparatus as claimed in claim 22, wherein the detector is embodied and arranged in such a way that it registers an extent of the at least one local temperature increase in the sample.

28. The apparatus as claimed in claim 22, wherein the detector is embodied and arranged in such a way that it registers a position of the at least one local temperature increase in the sample.

29. The apparatus as claimed in claim 28, wherein the detector is embodied and arranged in such a way that it registers the centroid of the position of the at least one local temperature increase in the sample with a spatial resolution that is better than the diffraction limit.

30. The apparatus as claimed in claim 22, wherein a temperature-regulating device for regulating the temperature of the sample to a temperature that can be set is provided.

31. The apparatus as claimed in claim 22, wherein the first signal source is embodied and arranged in such a way that it sets, by means of the first optical signal, a spatial distribution of a portion of the substance in the first state in the case of which only those portions of the substance which are situated at the location of a zero of the first signal that is formed by destructive superposition are in the first state.

32. The apparatus as claimed in claim 22, wherein the first signal source is embodied and arranged in such a way that it sets, by means of the first optical signal, a spatial distribution of a portion of the substance in the first state in the case of which only individual molecules or clusters of molecules of the substance are in the first state which are spaced apart from one another to such an extent that the detector detects the local temperature increases in the sample which proceed from them when the second signal is applied to the substance spatially separately from one another in an imaging.

33. The apparatus as claimed in claim 22, wherein a fluorescent light detector for the additional spatially resolved detection of fluorescent light from the sample is provided.

34. The apparatus as claimed in claim 22, wherein the first signal source is embodied and arranged in such a way that it applies the second electromagnetic signal to the sample in pulses having a high intensity density, and wherein the detector is embodied and arranged in such a way that it detects the temporary local temperature increase in the sample directly after each pulse of the second electromagnetic signal.

* * * * *